United States Patent
Al-Rasheed

(10) Patent No.: US 6,458,087 B1
(45) Date of Patent: Oct. 1, 2002

(54) PILLOW THERMOMETER

(76) Inventor: Abdullah K. Al-Rasheed, P.O.B. 3643, Riyadh (11481) (SA)

( * ) Notice: Subject to any disclaimer, the term of this patent is extended or adjusted under 35 U.S.C. 154(b) by 49 days.

(21) Appl. No.: 09/672,419

(22) Filed: Sep. 28, 2000

(51) Int. Cl.$^7$ ................................................ A61B 5/00
(52) U.S. Cl. .................................................... 600/549
(58) Field of Search ................................. 600/549, 595, 600/483, 500, 537, 300; 5/639, 636, 637, 904

(56) References Cited

U.S. PATENT DOCUMENTS 3,999,537 A  12/1976  Noiles ........................ 600/595
5,964,720 A  10/1999  Pelz .......................... 600/595

*Primary Examiner*—Kevin Shaver
*Assistant Examiner*—Brian Szmal
(74) *Attorney, Agent, or Firm*—Seto Patents; Jeffrey K. Seto

(57) ABSTRACT

One or more small metallic temperature sensors are attached to a pillow or pillowcase. Since the human head has a rich blood supply and human hair is not a significant insulator of heat, accurate temperature monitoring is achieved while the patient is sleeping. A wire attaches the sensor to a temperature monitoring unit. The monitor reads and stores the patient's temperature and sounds an alarm when the patient's temperature rises above a preset value, such as 98.5 F. The monitor can be placed in the patient's room or it can be located in another room. In cases where the "patient" is a child at home, the monitor can advantageously be place in the parent's room.

6 Claims, 2 Drawing Sheets

PILLOW THERMOMETER

BACKGROUND OF THE INVENTION

The present invention relates generally to the field of medical diagnostics and more specifically to a non-invasive temperature monitor for a sleeping patient.

One of the most important medical diagnostic tools in a doctors arsenal is the monitoring of a patient's temperature. When a patient has a temperature above normal, it is an indication to the doctor that there is something medically wrong with the patient. This important illness indicator will tell the doctor he should make further inquiries and/or do further tests to determine what exactly the problem is with the patient.

Taking the temperature of a patient is usually done orally or anally when the patient is awake. A conventional mercury or iodine filled glass thermometer is well suited for such temperature taking methods. Recently, an electronic thermometer has been introduced that takes the patient's temperature by inserting a short tubular piece attached to the thermometer into the patient's ear for several seconds. This hand held electronic thermometer shortens the required time period that the thermometer must be held in place before an accurate temperature may calculated. However, the hand held electronic thermometer shares similar disadvantages as those of the conventional glass thermometers. Each of the above methods of taking temperature is semi-invasive and a doctor, nurse or other person usually must handle or otherwise assist in the taking and monitoring of the patient's temperature. Even though it is possible for a patient to take their own temperature, this requires the patient to be awake and have access to and knowledge of the thermometer that is used.

These traditional methods of taking a temperature do not provide for automatic monitoring of the patient's temperature while the patient is sleeping. Each method requires a doctor or nurse or the patient himself to administer the temperature test at night when the patient would normally be asleep. The above conventional methods require multiple tests that must be repeated in short intervals to provide continuous monitoring of the patient's temperature.

Continuous temperature monitoring is necessary to detect illnesses as early as possible in patient's that are immuno-compromised or are susceptible to recurrent febrile (fever related) illnesses. Patients with an immune system that for some reason or another is not operating normally is said to be immuno-compromised. These patient's must prevent illnesses because their bodies no longer have their full ability to fight back against illnesses. Since a fever is usually one of the first symptoms of an oncoming illness, automated nighttime monitoring provides a great benefit to these patient's. Continuous night time temperature monitoring is also desirable for young children, especially those that suffer from febrile illnesses that could lead to febrile convulsions. Febrile convulsions occur in almost 2% of children below six years of age. The current state of the art for prophylaxis is to prevent recurrence of febrile convulsions which means preventing the precipitating fever or to use prophylactic oral diazepam during the febrile episode (1). Some children may even seize with only a minimal elevation in temperature, before the parent recognizes the symptoms of a fever. Further, children who suffer from febrile convulsions do not respond well to anticonvulsive drugs, which unfortunately can also cause serious side effects. Therefore, early detection of an oncoming fever is quite desirable and could also save the child's life Sometimes, a mild fever is overlooked by parent in the morning and few hours later the school or the day care calls and informs the family that their child is sick and the family needs to come and pick up the child.

Sleep represents one third of the life of children and most adults. Some children sleep 8–10 hours a day. During the day, children are observed and symptoms of a fever are more likely to be noticed than during the night time. The present invention monitors the temperature non-invasively during the night time in a way that allows it to be used on a daily basis, all year long. In an alternative embodiment, a parent can use a receiver/microphone to receive a temperature alarm (buzzing) transmission from the monitor.

Another method to measure the body temperature was a plastic strip thermometer that had to be affixed to the patient's forehead. This method brought about conflicting results. In one clinical trial published in JAMA (2), its accuracy was affected by variations in ambient air temperature. The conclusion of this study was that the method is unacceptable as a substitute for the mercury/glass thermometer. The medical consensus is that the forehead temperature is not as accurate as the other mode of temperature taking (i.e., rectal, oral, axially and aural). None of the traditional temperature taking methods mentioned above provide long term continuous non-invasive automated monitoring of a patient's temperature. What is needed is a non-invasive method for monitoring of a patient's temperature so that monitoring can automatically take place when the patient is asleep or napping.

The present invention solves the above problem by providing one or more temperature sensors that are attached to a patient's pillow or pillowcase. The human head has a rich blood supply and human hair is not a significant insulator of heat. This allows accurate temperature taking from a patient's head. A wire attaches the sensor to a temperature monitor. The monitor reads and stores the patient's temperature and sounds an alarm when the patient's temperature rises above a preset temperature, such as 98.5 F. The monitor can be placed in the patient's room or it can be located in another room. In the case where a child is the "patient", the monitor can advantageously be place in the parent's room. In this way, the parent would be alerted immediately when the child's temperature begins to rise above normal. The parent could then take defensive actions to try to bring down the child's temperature, such as cold sponges, removal of heavy clothing, antipyretics and possibly antibiotics. In the traditional temperature taking methods, the parent would not know of a fever that developed overnight in their child until the morning. This late diagnosis of a fever could be detrimental to children that suffer from febrile convulsions.

Metallic temperature sensors provide accurate temperature calculations based on the dynamic resistive properties of the metal. As the temperature of the metal changes, the resistivity of the metal changes. When a small electrical current is sent to the metal, the resistance of the metal can be calculated based on the current that comes out of the metal. Resistance values are matched to temperature values dependant upon the type of metal that is used in the thermometer. Platinum is known as an extremely accurate metal for use in electrical resistance thermometers. However, other metals such as copper, stainless steel and nickel are suitable substitutes.

SUMMARY OF THE INVENTION

In the preferred embodiment, one or more thin pieces of metal that act as electrical resistance thermometers are attached to a pillow or pillowcase that a patient will use to rest her head on. The metallic thermometer(s) are electrically connected to a monitor unit that has a display and memory. The monitor unit selectively displays current temperature or past temperatures with corresponding times. The monitor unit also has an alarm that sounds when the patient's temperature rises above a preset value. The present invention may be used when the patient goes to bed at night and in many cases the patient may be a young child and the person listening for the alarm may be the child's parent.

BRIEF DESCRIPTION OF THE DRAWINGS

The invention of the present application will now be described in more detail with reference to the accompanying drawings, given only by way of example, in which.

DETAILED DESCRIPTION OF THE INVENTION

Figure 1:
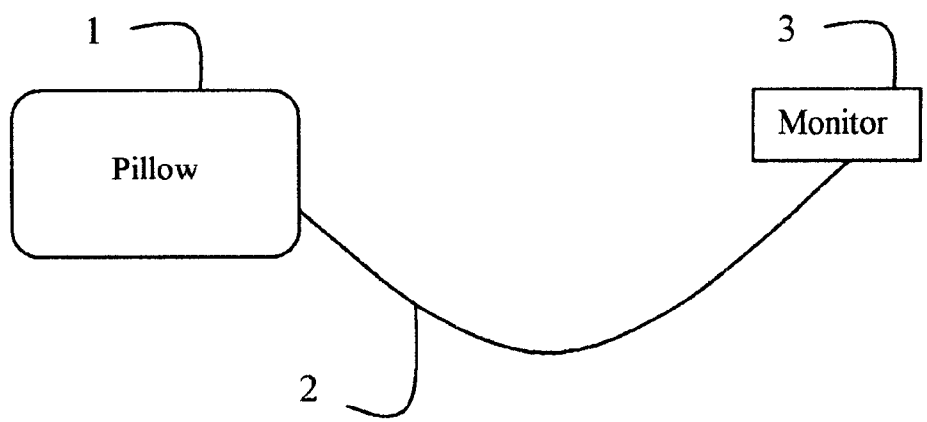
FIG. 1 is a block diagram of the preferred embodiment.

Referring to FIG. 1, pillow 1 comprises a traditional pillow with pillowcase that has been laced with one or more thin metallic temperature sensors. The sensors can be sewn into the fabric of the pillow or the pillowcase. Alternatively, the sensors can be attached with Velcro or placed within pockets made available on the pillow or pillowcase. The sensor(s) are electrically connected 2 to monitor unit 3. Monitor unit 3 may be in the same room as a patient/child or in another room. Monitor 3 comprises circuitry for storing and displaying values that correspond to temperature measurement of the patient/child. One of the most important features of monitor 3 is speaker that produces an audible alarm when the patient's/child's temperature goes above a preset value, such as 98.6 degree F.

Figure 2:
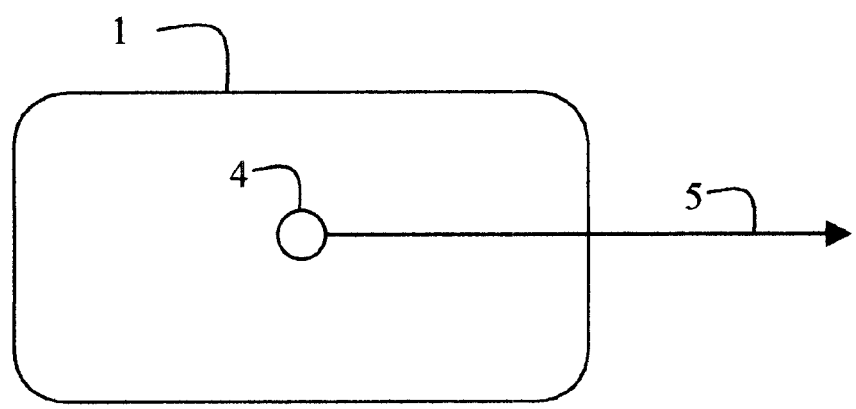
FIG. 2 is a detailed diagram of the pillow of the preferred embodiment.

FIG. 2 shows the thin electronic thermometer 4 attached to pillow 1. Electrical connection 5 continues to monitor 3 (not shown). Electrical connection 5 is an electrical wire in the preferred embodiment, however other connections could be used. In operation, a small electrical current is sent from monitor unit 3 to thermometer 4 via electrical connection 5. The amount of return electrical current from thermometer 4 is related to the resistance of thermometer 4. The resistance of thermometer 4 is related to the temperature of thermometer 4. Finally to complete the logic, the temperature of thermometer 4 is related to the temperature of the patient/ child. Thermometer 4 is not active if the perceived temperature is less than 95 degrees F. With thermometer 4 it is possible to measure temperature on a daily basis while the patient is sleeping or napping, wherein thermometer 4 in direct contact with the head. The present temperature taking method acts as a screener for high temperatures all year long. Some of the reasons why the present method can provide accurate temperature readings are because: the scalp contains a rich blood supply; hair is not a significant isolator of heat; usually, the head is stationary during sleep; and the present invention is easy to use and non-invasive.

Figure 3:
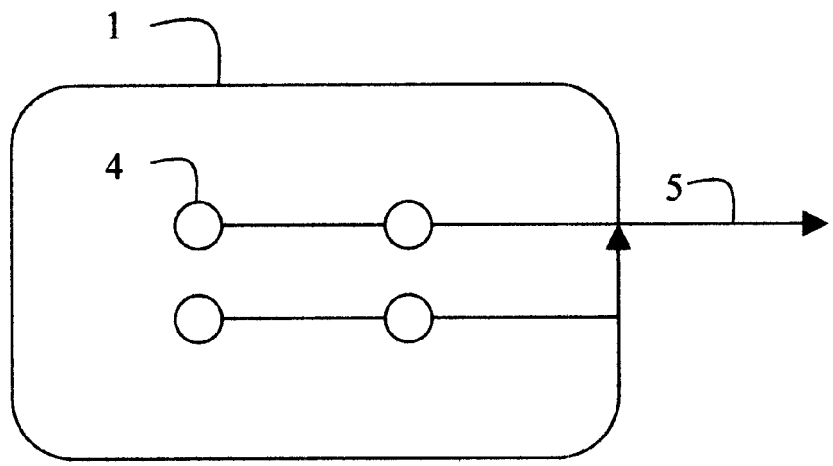
FIG. 3 is an alternative embodiment of the pillow.

FIG. 3 shows an alternative embodiment of the pillow 1. In this embodiment, each of the thermometers attached to pillow 1 is a duplicate of the thermometer 4 shown in FIG. 2. In this example, four thermometers are attached to pillow 1, however any number of thermometers could be attached. Further, the shape of thermometer 4 could be other than round. Each thermometer 4 in FIG. 3 is electrically connected to monitor unit 3 by electrical connection 5. In the preferred embodiment, the highest temperature recorded by any one of the thermometers 4 is the one temperature recorded by monitor 3. Alternatively, multiple wires could be provided in connection 5 and selective thermometer readings could be attained. Further in the preferred embodiment, thermometer 4 is a small round stainless steel sensor that starts to record when it senses a heat source above 95 degrees F and the temperature is displayed after a ten minute period to minimize the effect of the room temperature on the final reading.

Figure 4:
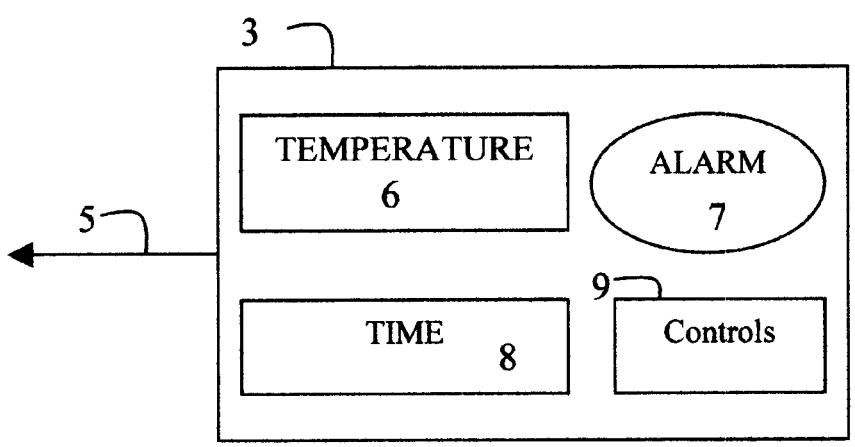
FIG. 4 is a detailed diagram of the monitor unit.

FIG. 4 is a detailed view of the monitor unit 3. The largest display is the temperature display 6. Alarm light 7 lights up or flashes when a preset temperature value has been detected, an audio alarm also sounds. Time display 8 shows the current time or a time corresponding to past temperature readings, which is useful when a user is displaying past temperature readings. Finally, monitor 3 is equipped with controls for turning the unit off and on, selecting the alarm threshold, displaying selected past temperature readings and controlling other features discussed in this application. In the preferred embodiment, the controls are well known push buttons and dials. Monitor unit 3 further comprises circuitry for translating received current values into temperature values and a memory to store the highest recorded temperatures on an hourly basis, for example. After the alarm 7 first sounds, which indicates a fever, you can either switch off the alarm or you change the threshold value so that only a moderate to high fever will triggers the alarm next. The monitor unit 3 is preferably battery powered. However, monitor 3 could also be powered via a typical 115V electrical outlet.

As mentioned above, a fever can indicate the presence of serious illness or infection. The earlier the fever is detected the early the interventions such as the use of antipyretics and tepid sponges can begin. Febrile convulsions cause severe panic in parents and could lead to detailed investigations such as a spinal tap that would require admission to the hospital, to rule out meningitis. Early recognition has paramount importance in children liable to having febrile convulsions or children with a compromised immune system.

There need only be at least one reading per night, which in the preferred embodiment requires only ten minutes out of a normal sleep period of eight hours. This translates to a mere 2% of the time the patient/child is asleep. Thus, there is a very high probability that the sensor will pick up at least one good reading from the head, the heat source, during the night. Generally, a person moves their head once during every sleep cycle and normally there are 4 . 6 sleep cycles per night. When there is a sudden decline in sensed temperature greater than 0.5 degrees F, for example, which can happen when the head moves away from the sensor, the sensor (thermometer) will stop recording. It will start recording again if there is temperature rise for a new ten minutes period.

The present invention could find useful employment as part of nursery, day care or hospital system to monitor the temperature of patient's that are not in an intensive care status. The present system is especially suited to the monitoring of children below six years of age who have frequent febrile illnesses and children and adults who are immuno-compromised.

The foregoing description of the specific embodiments will so fully reveal the general nature of the invention that others can, by applying current knowledge, readily modify and/or adapt for various applications such specific embodiments without departing from the generic concept. For instance, pillow 1 could have a wireless connection to monitor 3. Therefore, such adaptations and modifications should and are intended to be comprehended within the meaning and range of equivalents of the disclosed embodiments. It is to be understood that the phraseology of terminology employed herein is for the purpose of description and not of limitation.

REFERENCES

1. Rosman N P, Colton T, Labazzo J, Gilbert P L, Gardella N B, Kaye E M, Van Bennekom C, Winter M R; A controlled trial of diazepam administered during febrile illnesses to prevent recurrence of febrile seizures; N Engl J Med 1993 July 8; 329(2):79–84
2. Lewit E M, Marshall C L, Salzer J E; An evaluation of a plastic strip thermometer; JAMA 1982 January 15; 247 (3):321–5

I claim:

1. A temperature monitoring system that provides non-invasive automated monitoring of a patient's temperature, comprising:
   one or more thermometers that are adapted to come into contact with the patient's head, the one or more thermometers being attached to a pillow case, wherein the patient sleeps or naps on the pillow case and the thermometer(s) measures the patient's temperature;
   a connector, connected to each thermometer, that transfers signals between the thermometer(s) and a monitoring unit, wherein the monitoring unit uses the signals from the thermometer(s) to calculate the patient's temperature, the monitoring unit comprising;
      a temperature display for displaying current or past temperature values;
      a time display for displaying time values corresponding to the temperature values;
      a visual and audio alarm that attracts the attention of a care giver through a light that may flash and an auditory alarm that can selectively be reset;
      circuitry for calculating, storing and displaying temperature values; and
      a memory for storing temperature related information.

2. The temperature monitoring system of claim 1, wherein each thermometer is a stainless steel electrical thermometer.

3. A temperature monitoring system that provides non-invasive automated monitoring of a patient's temperature, comprising:
   one or more thermometers that are adapted to come into contact with the patient's head, the one or more thermometers being attached to a pillow, wherein the patient sleeps or naps on the pillow and the thermometer(s) measures the patient's temperature;
   a connector, connected to each thermometer, that transfers signals between the thermometer(s) and a monitoring unit, wherein the monitoring unit uses the signals from the thermometer(s) to calculate the patient's temperature, the monitoring unit comprising;
      a temperature display for displaying current or past temperature values;
      a time display for displaying time values corresponding to the temperature values;
      a visual and audio alarm that attracts the attention of a care giver through a light that may flash and an auditory alarm that can selectively be reset;
      circuitry for calculating, storing and displaying temperature values; and
      a memory for storing temperature related information, wherein the pillow is inside a pillow case and there are corresponding holes in the pillow case wherein the thermometer(s) is adapted to come into contact with the patient's head through the holes in the pillow case.

4. A method for non-invasive monitoring of a patient's temperature, the method involving the use of a pillow and a pillow case that the patient sleeps or naps on, comprising the steps of:
   attaching one or more thermometers to the pillow case;
   having the patient sleep on the pillow case;
   sending temperature information from the thermometer(s) to a monitoring unit;
   calculating the patient's temperature in the monitoring unit based on the information received from the thermometer(s);
   storing temperature and corresponding time values in a memory;
   displaying temperature and time values on the monitoring unit; and
   sounding an alarm when a calculated temperature is above a preset value.

5. The method of claim 4, further comprising the step of:
   making the thermometer(s) out of stainless steel.

6. The method of claim 4, wherein the step of attaching one or more thermometers comprises attaching the thermometer(s) to the pillow itself.

* * * * *